US008202526B2

(12) United States Patent  
Schaller

(10) Patent No.: US 8,202,526 B2  
(45) Date of Patent: Jun. 19, 2012

(54) PROPHYLACTIC ARTICLE

(75) Inventor: Raimund Schaller, Neunkirchen (AT)

(73) Assignee: Semperit Aktiengesellschaft Holding, Vienna (AT)

( * ) Notice: Subject to any disclaimer, the term of this patent is extended or adjusted under 35 U.S.C. 154(b) by 395 days.

(21) Appl. No.: 12/389,115

(22) Filed: Feb. 19, 2009

(65) Prior Publication Data

US 2009/0320179 A1 Dec. 31, 2009

Related U.S. Application Data

(60) Provisional application No. 61/030,350, filed on Feb. 21, 2008.

(30) Foreign Application Priority Data

Feb. 21, 2008 (AT) .................................. A 279/2008

(51) Int. Cl.  
*A01N 25/34* (2006.01)  
*A61K 9/48* (2006.01)

(52) U.S. Cl. ........................................ 424/402; 424/451

(58) Field of Classification Search .................. None  
See application file for complete search history.

(56) References Cited

U.S. PATENT DOCUMENTS

| 4,375,480 A | * | 3/1983 | Soma ............................ 514/772 |
| 4,533,487 A | * | 8/1985 | Jones ............................ 510/405 |
| 4,775,372 A | | 10/1988 | Wilberg |
| 4,930,522 A | | 6/1990 | Busnel et al. |
| 5,024,852 A | | 6/1991 | Busnel et al. |
| 5,559,149 A | * | 9/1996 | Clum et al. .................... 514/529 |
| 5,670,540 A | * | 9/1997 | Horrobin et al. .............. 514/549 |
| 6,274,154 B1 | | 8/2001 | Chou |
| 2002/0022040 A1 | * | 2/2002 | Robinson et al. ............. 424/401 |
| 2004/0170670 A1 | * | 9/2004 | Smith et al. ................... 424/443 |
| 2005/0002995 A1 | * | 1/2005 | Schaller ........................ 424/443 |
| 2005/0019351 A1 | * | 1/2005 | Belmar et al. ................. 424/401 |
| 2005/0051419 A1 | * | 3/2005 | Zima et al. ..................... 203/43 |
| 2005/0106201 A1 | | 5/2005 | Janssen |
| 2008/0040834 A1 | | 2/2008 | Schaller et al. |
| 2008/0268005 A1 | * | 10/2008 | Falkowski et al. ............ 424/401 |

FOREIGN PATENT DOCUMENTS

| AT | 413471 B | 3/2006 |
| AT | 503090 A1 | 7/2007 |
| DE | 3872629 T2 | 12/1992 |
| DE | 20100269 U1 | 8/2001 |
| EP | 306389 B1 | 7/1992 |
| WO | 03/022962 | 3/2003 |
| WO | 2005/036996 | 4/2005 |
| WO | WO 2007068372 A1 * | 6/2007 |

* cited by examiner

*Primary Examiner* — Robert A Wax  
*Assistant Examiner* — William Craigo  
(74) *Attorney, Agent, or Firm* — Greenblum & Bernstein, PLC

(57) ABSTRACT

The invention relates to a prophylactic article with a carrier element, which comprises at least in part a natural or synthetic elastomer, and with a combination of active substances that is contained in microcapsules, wherein the microcapsules are arranged at least in part in and/or on the carrier element. The combination of active substances contains at least one skin care agent, at least one preservative, at least one odor-inhibiting agent and at least one antioxidant.

27 Claims, No Drawings

PROPHYLACTIC ARTICLE

CROSS REFERENCE TO RELATED APPLICATIONS

This application claims priority under 35 U.S.C. 119 to Provisional Application No. 61/030,350, filed Feb. 21, 2008 and Austrian Application No. A 279/2008, filed Feb. 21, 2008, the contents of which are incorporated by reference in their entirety herein.

BACKGROUND OF THE INVENTION

1. Field of the Invention

The invention relates to a prophylactic article, in particular a glove, with a carrier element, which comprises at least in part a natural or synthetic elastomer, and with a combination of active substances that is contained in microcapsules, wherein the microcapsules are arranged at least in part in and/or on the carrier element, in particular in the area of the inner surface facing towards the carrier.

Medical gloves, whether in the form of examination gloves or in the form of operation gloves, have now become standard equipment for medical care. It is problematic hereby that the user's skin may react with irritation or allergically to the various elastomer materials if gloves of this type are worn over a longer period. In order to avoid this, it has already been proposed in the prior art to apply various active ingredients to the skin via the glove.

2. Prior Art

Thus, for example, a therapeutic glove is known from U.S. Pat. No. 6,274,154 B1, which has on its inner surface a layer of dehydrated aloe vera.

Similar to this, U.S. Pat. No. 4,775,372 A describes a glove containing aloe vera oil, wherein the oil is arranged between two layers of flexible plastic. However, the disadvantage hereby is that one of the layers must be punctured to apply the oil, whereby the glove not only loses its strength at least in some areas, but the danger is also associated therewith that substances from outside penetrate into the user's skin.

The microencapsulation of active substances has also been described in the prior art, e.g., in DE 201 00 269 U1 or in the applicant's AT 413 471 B or AT 503 090 A.

OBJECTS AND ADVANTAGES OF THE INVENTION

Since the capacity of microcapsules is naturally very small, it is important that the active substances contained therein are absorbed by the skin of the wearer of the gloves as quickly and completely as possible.

This object of the invention is therefore to provide a glove that has improved skin care properties.

The object of the invention is attained through the prophylactic article mentioned at the outset, in which the combination of active substances contains at least one skin care agent, at least one preservative, at least one odor-inhibiting agent and at least one antioxidant, wherein the at least one skin care agent is selected from a group comprising triglycerides of coconut fatty acids, avocado oil, jojoba oil, olive oil, cyclomethicone, squalane, borage oil, shea butter, macadamia oil, the at least one preservative is selected from a group comprising benzyl alcohol, benzyl benzoate, potassium sorbate, sodium hydroacetate, the at least one odor-inhibiting agent is selected from a group comprising citral, cumarin, citronellol, lilial, linalool, limonene, the at least one antioxidant is selected from a group comprising tocopheryl acetate, ascorbyl palmitate, betacarotene, oil of rosemary, and wherein the groups also comprise at least partially hydrated representatives or extracts of the cited active substance.

In the course of the further development of the applicant's product according to the two documents cited above for the prior art, it was surprisingly found that the new combination of active substances not only is particularly well tolerated by the skin, but also penetrates quickly into the skin of the user of the prophylactic article. In combination with the microencapsulation, a prophylactic article is obtained which supplies its active substances, i.e., the skin care substances, to the user over a very long period, since the microcapsules do not all break open at the same time, in particular when the gloves are drawn on, but the active substances are only gradually released due to the constant mechanical stress of the gloves. The conditioning effect is thus maintained over a longer period, wherein through the quick absorption of the active substances into the skin hardly any loss or no loss at all of active substances occurs. It is thus possible to reduce the proportion of active substances in the entire glove, compared to complete coatings of gloves, wherein the gloves can be produced more cost-effectively compared to the prior art products with coatings. It was furthermore established that these substances can be microencapsulated particularly well, whereby the production method per se can be designed in a more cost-effective manner, whereby in turn positive effects on the initial costs of the prophylactic article result. Through the addition of a preservative and at least one antioxidant, this combination of active substances is given an increased storage quality so that the prophylactic articles still develop their full effect even after longer storage time. With the aid of the odor-inhibiting agent, which acts on odor molecules in a masking manner, on the one hand it is achieved that the basic odor of the product itself can be at least almost neutralized, on the other hand this agent also develops its effect during the wearing of the prophylactic article. Odor formation due to sweating by the wearer—since this is a prophylactic article, it must be impermeable for liquids and gases—can be prevented. Through the application of the skin care agent, the skin of the wearer of the prophylactic article becomes softer and is smoothed, which is important in particular with respect to the development of the prophylactic article as a medical glove, since through the frequent washing of hands, which doctors, in particular surgeons are instructed to do, the hands often tend to dry out.

According to an embodiment variant of the invention it is provided that the preservative(s), the odor-inhibiting agent(s) and the antioxidant or antioxidants in total are contained in a proportion of no more than 10% by weight and the skin care agent(s) form the rest. It is particularly preferred thereby if this total preparation is no more than 5% by weight. This reduction of these ingredients of the combination of active substances is possible, since the combination of active substances is microencapsulated, i.e., the active ingredients are already protected per se by the capsule casing. It is thus possible to increase the skin care proportion of the combination of active substances accordingly, whereby not only can the skin care effect of the prophylactic article equipped therewith be increased, but through the reduction of the substances acting "more aggressively" compared to the skin care agents—a possible skin intolerance is better combated.

It can furthermore be provided that the combination of active substances contains at least one humectant factor, which is selected from a group comprising bisabolol, fructose, inositol, nicotinamide, sodium lactate. A better tolerance for users with relatively dry skin is achieved through this further development of the prophylactic article. In turn, it is advantageous with the selected humectant factors that they develop their effect very quickly and, moreover, no disturbing interactions with the skin care agents occur, whereby the processability, in particular the microencapsulation, is improved. Furthermore, any discomfort on the skin that may possibly occur, the prophylactic articles normally lie very closely on the skin, can thus be relieved—in particular with gloves, sizes are often used that is one size smaller than would correspond to the hand size, in order to improve the tactility.

Through the quick availability of the humectant factor, the proportion thereof in the combination of active substances in turn can be kept very low, so that this proportion of the humectant factor or humectant factors in total can be no more than 3% by weight, preferably no more than 1.5% by weight.

It should be noted at this point that all of the further active substances that are contained in addition to the skin care agent, the odor-inhibiting agent, the antioxidant or the preservative in the prophylactic article, cause a reduction of the proportion of the skin care agent or a reduction of the proportion of preservative, antioxidant and odor-inhibiting agent.

Furthermore, the combination of active substances can contain geraniol, whereby a pleasant feeling on the skin can be generated during the wearing of the prophylactic article, so that the wearability of the prophylactic article is thus improved over a longer period.

The proportion of geraniol in the combination of active substances can thereby preferably be no more than 0.3% by weight, in particular no more than 0.1% by weight, since the combination of active substances according to the invention per se already has a very good skin tolerance and thus an irritating feeling on the skin that may occur is already reduced.

The combination of active substances can contain at least one further active substance selected from a group comprising allantonin, *arnica* extract, oat extract, *calendula* oil, chamomile extract, ethylhexyl stearate, azulene. The prophylactic articles can thus be given to a certain extent a skin regenerating, blood-flow stimulating, antipruritic effect. The dispersibility of the combination of active substances on the skin is improved in particular through ethylhexyl stearate.

The proportion of the at least one further active substance in the combination of active substances can be in total preferably no more than 10% by weight, in particular no more than 5% by weight, preferably 2.5% by weight.

It is further possible to add at least one perfume to the combination of active substances in order to cover their inherent odor or in order to provide the prophylactic article in different perfume variations.

To improve the encapsulability of this combination of active substances, it is provided according to one embodiment variant that it is diluted with a triglyceride and a perfume, wherein the proportion of the triglyceride is selected from a range with a lower limit of 10% by weight and an upper limit of 20% by weight, preferably with a lower limit of 12% by weight and an upper limit of 16% by weight, the proportion of the perfume is selected from a range with a lower limit of 5% by weight and an upper limit of 15% by weight, preferably from a range with a lower limit of 8% by weight and the upper limit of 12% by weight, the combination of active substances forming the rest.

This perfume can thereby be formed by lavender oil, whereby not only the oil character of the combination of active substances is increased, but also the prophylactic article is given an antiseptic and calming effect due to the action of the lavender oil.

To make it easier to draw on the prophylactic article, in particular in the embodiment as a medical glove, the carrier element can have a sliding layer on a surface, i.e., the inner surface of the glove, since, as already mentioned, medical gloves are embodied to fit very closely and thus problems regarding the sliding property of the elastomer on the skin can occur, particularly when they are drawn on with wet hands.

It is advantageous thereby if the microcapsules at least in part are arranged in and/or on the sliding layer, whereby the application of the combination of active substances is also improved with this embodiment variant. Also in this case additionally microcapsules can be arranged below the sliding layer, i.e., at least in part in and/or on the elastomer of the carrier element, or there is a possibility that the microcapsules are arranged exclusively in and/or on the sliding layer.

Preferably the combination of active substances has an at least approximately oily consistency, in particular this combination of active substances is a skin protection oil, whereby the application of the active ingredients in deeper regions of the skin takes place more quickly and thus in turn a reduction of the proportion of the combination of active substances in the prophylactic article can be achieved.

In order to achieve a high lipid penetration capacity of the combination of active substances or individual constituents thereof, it is advantageous if this combination of active substances has a viscosity at 37° C. of no more than 250 mPas, in particular no more than 100 mPas and/or the combination of active substances has a saponification value according to DIN 53401 of no more than 250, in particular no more than 150 and/or the proportion of triglyceride skin care agents in the combination of active substances is no more than 50% by weight, preferably no more than 30% by weight. As known, the saponification value is a measurement of the bound and free acids occurring in 1 g fat. It shows how many mg of a lye are necessary in order to neutralize the free acids contained in 1 g fat and to split the ester compounds present. The reduction of the proportion of triglyceride skin care agent means that the molecular configuration of the active substances preferably has straight chains and branched esters, which penetrate better than triglyceride oils. In turn, through these measures a reduction of the proportion of the combination of active substances in the prophylactic article is achieved, whereby in addition to the reduction in costs a high safety of the application of active substances can be obtained, in the event that the individual microcapsules do not burst and thus do not release the active ingredients. Furthermore, the proportion of the microcapsules can thereby be reduced, whereby the homogenization thereof in the elastomer during the production of the prophylactic article can be facilitated.

DETAILED DESCRIPTION OF PREFERRED EMBODIMENTS

For a better understanding of the invention, it is explained in more detail based on the following description.

The prophylactic article according to the invention in addition to gloves, in particular medical operation or examination gloves, can also be condoms, finger stalls or protective gloves for work in cleanroom areas, etc. Prophylactic articles of this type have already been adequately described in the applicant's AT 413 471 B or AT 503 090 A with respect to their composition regarding the elastomer, i.e., the natural or synthetic latices, e.g., natural rubber, neoprene, synthetic polyisoprene, nitrile-butadiene and styrene-butadiene rubber, or a mixture thereof, and regarding the optionally arranged sliding layer, wherein this sliding layer can be formed by a sliding film, for example, a silicone oil, but also from the latex itself, for example through halogenation, such as, e.g., chlorination, or by certain surface modifications and designs, also with respect to the microcapsules used, in particular the size in the range between 0.1 μm to 100 μm, wherein in the scope of the present invention microcapsules are preferably used which have a size selected from a range between 0.1 μm and 10 μm, as with respect to the capsule material itself, wherein here preferably a polymer on a melamine-formaldehyde basis, e.g., according to DE 29 40 786 A is used. The application of the microcapsules themselves on or in the prophylactic article through the production of corresponding suspensions or emulsions from the latices, has already been dealt with extensively in these documents, so that a more detailed discussion is not necessary at this point and reference is therefore made to these two documents for these points of the invention, which in this respect are therefore part of the content of the present invention.

Preferably the prophylactic articles are produced in a dipping process with corresponding dipping forms. However, these can also be, e.g., sprayed, etc.

The microencapsulation of the combination of active substances, in particular of the oil, has the advantage that active substances can thus also be used, which are incompatible or compatible only to a lesser extent with respect to the carrier material or a possibly present sliding layer. In other words, the microcapsules have a protective function for the active substance(s) of the prophylactic article. Moreover, the oil can thus be prevented from diffusing into the prophylactic article and thus is available for the actual function only to a reduced extent. It is therefore achieved thereby that the combination of active substances is better available for the wearer's skin.

The ingredients of the combination of active substances provided according to the invention have already been sufficiently described above. At this point, therefore, only the individual effect will be briefly described, wherein it is noted that these are conventional active substances, which are used in the cosmetics industry and thus the action thereof per se has already been adequately documented.

Triglycerides of Coconut Fatty Acids (Caprylic/Capric Triglycerides):
This active ingredient makes the skin supple and smoothes it. Moreover, it makes it possible to easily distribute the combination of active substances on the skin. The preferred proportion in the combination of active substances is between 25% by weight and 50% by weight, or between 30% by weight and 40% by weight.

Avocado Oil (*Persea gratissima*):
This active ingredient makes the skin supple and smoothes it. Moreover the skin is protected from dryness and chapping. The preferred proportion is between 10% by weight and 25% by weight or between 15% by weight and 20% by weight.

Jojoba Oil (*Simmondsia chinensis, Buxus chinensis*):
This active ingredient also makes the skin supple and smoothes it, without visibly greasing. The preferred proportion is 10% by weight and 30% by weight or between 15% by weight and 20% by weight.

Olive Oil (*Olea europaea* Fruitoil):
Olive oil has a high proportion of unsaturated fatty acids for strengthening the skin barrier. This active ingredient also makes the skin supple and smoothes it. The preferred proportion is between 10% by weight and 25% by weight or between 15% by weight and 20% by weight.

Cyclomethicone:
Again this active ingredient—it is a type of silicone oil—has a smoothing effect on the skin and makes it supple. Furthermore, cyclomethicone has an antistatic effect, whereby the production of the microcapsules can be improved, a film-forming, viscosity-regulating and moisturizing effect. This is also a moisturizing factor. The preferred proportion is between 1% by weight and 5% by weight, or 2% by weight and 3% by weight.

Squalane:
In addition to the effect that this active substance makes the skin supple and smoothes it, squalane has a regreasing effect, in general conditioning for the skin. It is an extract of olive oil. The preferred proportion is between 1% by weight and 5% by weight or between 2% by weight and 3% by weight, but in individual exemplary embodiments can also be up to 20% by weight.

Borage Oil (*Borago officinalis*/Borage Se):
Borage oil makes the skin supple and smoothes it. The preferred proportion is between 1% by weight and 5% by weight or between 2% by weight and 3% by weight, but in individual exemplary embodiments can also be up to 25% by weight.

Shea Butter (*Butyrospermum parkii*):
Shea butter or a liquid extract thereof has a particularly marked conditioning and skin-friendly effect. The preferred proportion is between 1% by weight and 5% by weight, in particular between 2% by weight and 3% by weight. However/the proportion can also be up to 40% by weight.

Macadamia Oil (*Macadamia temifolia*):
Macadamia oil has an excellent conditioning effect, since it is rich in unsaturated fatty acids. The preferred proportion is between 1% by weight and 5% by weight or between 2% by weight and 3% by weight. However, the proportion can also be up to 40% by weight.

Benzyl Alcohol:
Benzyl alcohol has a preservative effect, primarily inhibits the development of microorganisms in the combination of active substances. Furthermore, benzyl alcohol gives the combination of active substances a jasmine-like scent. The preferred proportion is up to a max. of 0.5% by weight, in particular up to a max. of 0.1% by weight.

Benzyl Benzoate:
Benzyl benzoate is a very well tolerated preservative and has a similar effect to benzyl alcohol, but without giving the combination of active substances a specific scent. The preferred proportion is up to a max. of 0.5% by weight or max. of 0.1% by weight.

Potassium Sorbate:
Potassium sorbate is used in particular for prophylactic articles that must have a particularly high tolerance level by the skin, i.e., in particular for gloves, the wearers of which quickly react to latices with a skin irritation. This is a mild preservative, which gives the combination of active substances longer durability. The preferred proportion is up to a max. of 0.5% by weight or a max. of 0.1% by weight.

Sodium Hydroacetate:
Sodium hydroacetate is likewise a preservative that is well tolerated, similar to potassium sorbate. The preferred proportion is in turn up a max. of 0.5% by weight or a max. of 0.1% by weight.

Citral, Cumarin, Citronellol, Lilial (Butylphenyl Methylpropional):
These active ingredients have a masking effect, prevent or inhibit the odor of the combination of active substances. The preferred proportion is up to a max. of 5% by weight or a max. of 0.5% by weight or a max. of 0.1% by weight for each of these active substances, if they are contained individually in the combination of active substances.

Linalool:
Linalool has a deodorizing effect. The preferred proportion is up to a max. of 0.5% by weight or up to a max. of 0.1% by weight.

Limonene:

Limonene has a skin-conditioning and odor-inhibiting effect. The preferred proportion is up to a max. of 0.5% by weight or up to 0.1% by weight.

Tocopheryl Acetate, Ascorbyl Palmitate, Betacarotene, Oil of Rosemary:

These are antioxidants, i.e., these active ingredients prevent individual constituents of the combination of active substances from oxidizing due to longer storage or also already during production and are thus impaired in their effect or prevent the odor from any odor-forming breakdown products of the combination of active substances that may develop. These are usually radical interceptors. The preferred proportion of each of these representatives of the antioxidants is up to a max. of 0.5% by weight or up to a max. of 0.1% by weight.

Bisabolol, Fructose, Inositol, Niacinamide, Sodium Lactate:

These active substances are humectant factors, i.e., they prevent the skin from drying out. Each of these active substances can preferably be present in a proportion of up to a max. of 3% by weight or up to a max. of 1% by weight, wherein these active substances in total are contained in a proportion of a max. of 3% by weight, if several of these humectant factors are used. The humectant factors can be contained in particular individually in a proportion of 0.1% by weight to 1% by weight.

Geraniol:

Geraniol has a strengthening effect and produces a pleasant feeling on the skin. Moreover it can be used for odor correction. The preferred proportion is up to a max. of 0.3% by weight or up to a max. of 0.1% by weight.

Allantonin, *arnica* Extract (*Arnica montana*), Oat Extract (*Avena sativa*), *calendula* Oil (*Calendula officinalis*), Chamomile Extract (*Chamomilla recutita*), Ethylhexyl Stearate, Azulene (Guajazulene):

Allantonin has a soothing effect on the skin and promotes the formation of tissues, i.e., it has a positive effect when the wearer of the prophylactic article has a superficial skin injury.

*Arnica* extract has a regenerating effect and stimulates the blood flow.

Oat extract has a mild conditioning effect, soothes the skin and is antipruritic.

*Calendula* oil has a skin soothing and regenerating effect in the case of chapped and cracked skin.

Chamomile extract is used in particular when the wearer of the prophylactic article has a very tender, sensitive skin.

Ethylhexyl stearate improves the dispersibility of the combination of active substances on the skin.

Azulene is a skin-soothing active substance, comparable to chamomile.

The preferred proportion of these active ingredients can be individually up to a max. of 10% by weight or up to 5% by weight or up to a max. of 2.5% by weight, wherein, if several of these active ingredients are contained, the total proportion in the combination of active substances is a max. of 10% by weight.

Perfume:

The combination of active substances is given a specific fragrance direction by perfume active substances and the basic odor of the combination of active substances can also be better covered thereby. The preferred proportion of perfume ingredients is up to a max. of 1.5% by weight or preferably between 0.1% by weight and 1% by weight.

In order to be better able to encapsulate the combination of active substances produced by mixing the individual ingredients, as already stated above, this skin protection oil can be diluted. In this respect, reference is made to the above statements.

Furthermore, extracts or at least partially hydrated representatives of these active substances can be used.

The combination of active substances can contain up to 98% by weight of at least one of the skin conditioning agents. In this case proportions of preservatives, odor-inhibiting agents and antioxidants are restricted to a total of a max. of 2% by weight. On the other hand it is possible for the combination of active substances to contain a max. of 90% by weight of skin conditioning substances, so that the other ingredients of the combination of active substances therefore have a proportion of a max. of 10% by weight.

The constituent amounts of the dilution relate to the entire combination of active substances, i.e., the relative proportions of the individual ingredients in the combination of active substances with respect to one another are not changed by the dilution.

Since it is not possible to list all of the combinations of active substances within the scope of this description, only the particularly preferred exemplary embodiments are listed below. The data given on the constituent amounts are thereby to be understood as % by weight. The respectively preferred ranges of the compounds are given in parentheses, within which the respective ingredients or active substances can be varied. The active substances are commercially available products.

Exemplary Embodiment 1

| | |
|---|---|
| Caprylic/capric triglycerides | 96.0% (94%-98%) |
| Benzyl alcohol | 0.5% (0.1%-0.5%) |
| Citronellol | 3.0% (0.1%-5%) |
| Ascorbyl palmitate | 0.5% (0.05%-0.5%) |

Exemplary Embodiment 2

| | |
|---|---|
| Shea butter extract | 37% (20%-40%) |
| Macadamia oil | 25% (10%-30%) |
| Jojoba oil | 28.5% (10%-25%) |
| Bisobolol or nicotinamide | 2.5% (0.1%-3.0%) |
| Ethylhexyl stearate | 2.5% (1.5%-6.0%) |
| Sodium hydroacetate | 0.5% (0.1%-0.5%) |
| Oil of rosemary | 0.5% (0.1%-0.5%) |

Exemplary Embodiment 3

| | |
|---|---|
| Avocado oil | 25% (15.0%-25.0%) |
| Macadamia oil | 31.7% (20.0%-35.0%) |
| Jojoba oil | 25% (15.0%-25.0%) |
| Perfume | 1% (0.1%-1%) |
| Geraniol | 0.3% (−0.3%) |
| Oat extract | 5% (1.5%-8.0%) |
| Calendula oil | 5.7% (1.5%-8.0%) |
| Sodium lactate | 3% (1.0%-3.0%) |
| Potassium sorbate | 0.3% (0.01-0.3%) |
| Ascorbyl palmitate | 0.5% (0.01-0.5%) |
| Betacarotene | 0.25% (0.01-0.3%) |
| Oil of rosemary | 0.25% (0.01-0.3%) |

Exemplary Embodiment 4

| | | |
|---|---|---|
| Caprylic/capric triglycerides | 96.0% | (25%-50%) |
| *Persea gratissima* | 14.0% | (10%-25%) |
| *Simmondsia chinensis* | 14.0% | (10%-25%) |
| *Olea europea* fruit oil | 11.45% | (10%-25%) |
| Cytomethicone | 2.75% | (1%-5%) |
| Squalane | 2.75% | (1%-5%) |
| *Borago officinalis*/borage SE | 2.75% | (1%-5%) |
| Perfume | 0.5% | (0.1%-1%) |
| Bisabolol | 0.5% | (0.1%-1%) |
| Tocopheryl acetate | 0.5% | (0.1%-1%) |
| Linalool | 0.1% | (−0.1%) |
| Limonene | 0.1% | (−0.1%) |
| Butylphenyl methylpropional | 0.1% | (−0.1%) |
| Citronellol | 0.1% | (−0.1%) |
| Cumarin | 0.1% | (−0.1%) |
| Geraniol | 0.1% | (−0.1%) |
| Citral | 0.1% | (−0.1%) |
| Benzyl alcohol | 0.5% | (0.1%-0.5%) |

Exemplary Embodiment 5

| | |
|---|---|
| Borage oil | 20.0% |
| Squalane | 20.0% |
| Avocado oil | 25.0% |
| Jojoba oil | 30.0% |
| Potassium sorbate | 0.5% |
| Cumarin | 1.0% |
| Lilial | 1.0% |
| Tocopheryl acetate | 0.5% |
| Inositol | 2.0% |
| Geraniol | 0.2% |
| Arnica extract | 0.1% |
| Allantonin | 0.1% |
| Perfume | 0.1% |

Exemplary Embodiment 6

| | |
|---|---|
| Macadamia oil | 40.0% |
| Olive oil | 25.0% |
| Squalane | 21.0% |
| Potassium sorbate | 0.5% |
| Sodium lactate | 3% |
| Geraniol | 0.2% |
| Chamomile extract | 10% |
| Perfume | 0.3% |

Microcapsules were produced with these combinations of active substances, optionally after the dilution described above, with a method according to the prior art for the microencapsulation of active substances. These microcapsules were subsequently added to a conventional elastomer compound corresponding to the prior art in a concentration of between 0.1% by weight and 10% by weight, based on the total latex dispersion. From this subsequently gloves were produced by means of a conventional dipping process, as is described, for example, in the applicant's two above-referenced documents from the prior art.

To evaluate the functional properties, gloves of this type with combinations of active substances according to the exemplary embodiments 1 through 6 were worn by respectively 100 test persons over a period of respectively 8 hours. Each of these test persons thereby wore respectively one glove according to exemplary embodiments 1 through 6. After the end of 8 hours, on the one hand, the skin of the test persons was visually evaluated, on the other hand, the subjective perception of these test persons was verified by means of questionnaires that did not reveal the respective identities and contained questions regarding itchy feeling during wear, etc. It turned out that virtually 100% of the test persons found a glove with a combination of active substances according to exemplary embodiment 4 the most pleasant to wear. Embodiments of a glove with combinations of active substances according to exemplary embodiments 1 through 3 and 5 and 6 were evaluated by between 97% and 99% of the test persons as very positive with regard to wearing comfort and the feeling on the skin. The visual evaluation of the skin after the gloves were removed from the hands of the test persons did not show a reddening of the skin in any of the cases.

The combinations of active substances according to exemplary embodiments 1 through 6 all have an oily consistency.

As already stated above, to increase the lipid penetration through the combination of active substances, i.e., individual constituents of this combination of active substances, the viscosity of this combination of active substances at 37° C. can have a value of a max. of 250 mPas and/or a saponification value according to DIN 53401 of no more than 250. To adjust these values the individual ingredients can be varied according to their proportion in the combination of active substances.

To further improve the lipid penetration, it is advantageous if the proportion of triglyceride skin conditioning agents in the combination of active substances is no more than 50% by weight.

All of the data on value ranges in this specification are to be understood to cover any and all partial ranges therefrom, e.g., 1-10 is to be understood in that all partial ranges starting from the lower limit 1 and the upper limit 10 are covered, i.e., all partial ranges begin with a lower limit of 1 or greater and end with an upper limit of 10 or less, e.g., 1 to 1.7, or 3.2 to 8.1 or 5.5 to 10.

The exemplary embodiments show possible embodiment variants of the prophylactic article, wherein it is noted at this point that the invention is not limited to the embodiment variants of the same specifically shown, but instead various combinations of the individual embodiment variants among one another are possible and this variation possibility based on the teaching for technical actions through the present invention lies within the ability of one skilled in the art in this technical field.

The invention claimed is:

1. Prophylactic article with a carrier element, comprising at least in part a natural or synthetic elastomer, and including a combination of active substances contained in microcapsules, wherein the microcapsules are arranged at least in part in and/or on the carrier element, the combination of active substances containing at least one skin care agent, at least one preservative, at least one odor-inhibiting agent and at least one antioxidant, the at least one skin care agent comprising at least one of triglycerides of coconut fatty acids, avocado oil, jojoba oil, olive oil, cyclomethicone, squalane, borage oil, shea butter, and macadamia oil; the at least one preservative comprising at least one of benzyl alcohol, benzyl benzoate, potassium sorbate, and sodium hydroacetate; the at least one odor-inhibiting agent comprising at least one of citral, cumarin, citronellol, lilial, linalool, and limonene; the at least one antioxidant comprising at least one of tocopheryl acetate, ascorbyl palmitate, betacarotene, and oil of rosemary; and the combination of active substances has a viscosity at 37° C. of no more than 250 mPas and a saponification value according to DIN 53401 of no more than 250.

2. Prophylactic article according to claim 1, wherein the at least one preservative, the at least one odor-inhibiting agent and the at least one antioxidant in total are contained in a proportion of no more than 10% by weight of the combination of active substances and the at least one skin care agent forms the remainder of the combination of active substances.

3. Prophylactic article according to claim 1 wherein the combination of active substances contains at least one humectant factor, the at least one humectant factor comprising at least one of bisabolol, fructose, inositol, nicotinamide, and sodium lactate.

4. Prophylactic article according to claim 3, wherein the at least one humectant factor in total is no more than 3% by weight of the combination of active substances.

5. Prophylactic article according to claim 1, wherein the combination of active substances contains geraniol.

6. Prophylactic article according to claim 5, wherein the geraniol comprises a maximum of 0.3% by weight of the combination of active substances.

7. Prophylactic article according to claim 1 wherein the combination of active substances contains at least one further active substance comprising at least one of allantonin, arnica extract, oat extract, calendula oil, chamomile extract, ethylhexyl stearate, and azulene.

8. Prophylactic article according to claim 7, wherein the proportion of the at least one further active substance in total is no more than 10% by weight.

9. Prophylactic article according to claim 1 wherein the combination of active substances contains at least one perfume.

10. Prophylactic article according to claim 1 wherein the combination of active substances is diluted with a diluent comprising triglyceride and a perfume, wherein a proportion of the triglyceride in the diluent is selected from a range with a lower limit of 10% by weight and an upper limit of 20% by weight, a proportion of the perfume in the diluent is selected from a range with a lower limit of 5% by weight and an upper limit of 15% by weight.

11. Prophylactic article according to claim 10, wherein the perfume is formed by lavender oil.

12. Prophylactic article according to claim 1, wherein the carrier element has a sliding layer on a surface.

13. Prophylactic article according to claim 12, wherein the microcapsules are arranged at least in part in and/or on the sliding layer.

14. Prophylactic article according to claim 1 wherein the combination of active substances has an at least approximately oily consistency.

15. Prophylactic article according to claim 1 wherein the proportion of triglyceride skin care agents in the combination of active substances is no more than 50% by weight.

16. Prophylactic article according to claim 1 comprising a glove.

17. Prophylactic article according to claim 2 comprising a glove.

18. Prophylactic article according to claim 3 comprising a glove.

19. Prophylactic article according to claim 1 wherein the combination of active substances comprises at least one at least partially hydrated active substance.

20. Prophylactic article according to claim 1 wherein the combination of active substances comprises at least one extract of at least one active substance.

21. A method of manufacturing a prophylactic article with a carrier element, comprising forming a carrier element at least in part of a natural or synthetic elastomer, and arranging microcapsules including a combination of active substances contained in microcapsules at least in part in and/or on the carrier element, the combination of active substances containing at least one skin care agent, at least one preservative, at least one odor-inhibiting agent and at least one antioxidant, the at least one skin care agent comprising at least one of triglycerides of coconut fatty acids, avocado oil, jojoba oil, olive oil, cyclomethicone, squalane, borage oil, shea butter, and macadamia oil; the at least one preservative comprising at least one of benzyl alcohol, benzyl benzoate, potassium sorbate, and sodium hydroacetate; the at least one odor-inhibiting agent comprising at least one of citral, cumarin, citronellol, lilial, linalool, and limonene; the at least one antioxidant comprising at least one of tocopheryl acetate, ascorbyl palmitate, betacarotene, and oil of rosemary; and the combination of active substances has a viscosity at 37° C. of no more than 250 mPas and a saponification value according to DIN 53401 of no more than 250.

22. Prophylactic article according to claim 1, wherein the combination of active substances has a viscosity at 37° C. of no more than 100 mPas.

23. Prophylactic article according to claim 22, wherein the combination of active substances has a saponification value according to DIN 53401 of no more than 150.

24. Prophylactic article according to claim 1, wherein the proportion of triglyceride skin care agents in the combination of active substances is no more than 50% by weight.

25. Method according to claim 21, wherein the combination of active substances has a viscosity at 37° C. of no more than 100 mPas.

26. Method according to claim 25, wherein the combination of active substances has a saponification value according to DIN 53401 of no more than 150.

27. Method according to claim 1, wherein the proportion of triglyceride skin care agents in the combination of active substances is no more than 50% by weight.

* * * * *